(12) United States Patent
Kawahara et al.

(10) Patent No.: US 9,511,124 B2
(45) Date of Patent: Dec. 6, 2016

(54) ANTI-ALLERGIC SUBSTANCE, ANTI-ALLERGIC AGENT, AND FOOD

(75) Inventors: Hiroharu Kawahara, Kitakyushu (JP); Yuichi Inoue, Kitakyushu (JP)

(73) Assignee: Institute of National Colleges of Technology, Japan, Tokyo (JP)

( * ) Notice: Subject to any disclaimer, the term of this patent is extended or adjusted under 35 U.S.C. 154(b) by 23 days.

(21) Appl. No.: 14/113,198

(22) PCT Filed: Apr. 17, 2012

(86) PCT No.: PCT/JP2012/060389
§ 371 (c)(1),
(2), (4) Date: Oct. 21, 2013

(87) PCT Pub. No.: WO2012/144501
PCT Pub. Date: Oct. 26, 2012

(65) Prior Publication Data
US 2014/0037690 A1    Feb. 6, 2014

(30) Foreign Application Priority Data

Apr. 22, 2011 (JP) ................. 2011-096512

(51) Int. Cl.
| | | |
|---|---|---|
| A61K 39/35 | (2006.01) | |
| A61K 39/36 | (2006.01) | |
| A61K 45/00 | (2006.01) | |
| A61K 47/00 | (2006.01) | |
| A61K 38/44 | (2006.01) | |
| A23L 1/30 | (2006.01) | |

(52) U.S. Cl.
CPC .............. *A61K 38/44* (2013.01); *A23L 1/3002* (2013.01); *C12Y 102/01012* (2013.01)

(58) Field of Classification Search
None
See application file for complete search history.

(56) References Cited

U.S. PATENT DOCUMENTS

2002/0159976 A1*  10/2002  Glenn ................. A23C 19/0323
424/93.2

FOREIGN PATENT DOCUMENTS

JP        2000-139404 A      5/2000

OTHER PUBLICATIONS

Pinto et al. 'Bioactive compounds and quantification of total ellagic acid in strawberries (Fragaria x ananassa Duch.)' Food Chem. 107:1629-1635, 2008.*
Iwamoto et al. 'Purification and identification of an IgE suppressor from strawberry in an in vitro immunization system.' Cytotechnol. 64:309-314, 2012.*
Iwamoto et al. 'Anti-allergic effect of strawberry extract.' J. Function. Foods. 5:1947-1955, 2013.*
Mitsuda et al. 'Detection of anti-allergic effects in strawberry extracts.' In: Kamihira M et al. (eds) Proceedings of the 21st annual and international meeting of the Japanese association for animal cell technology, Fukuoka, Nov. 2008. Animal Cell Technology: Basic & Applied Aspects vol. 16, pp. 353-357, 2010.*
Rosenfeldt et al. 'Effect of probiotics on gastrointestinal symptoms and small intestinal permeability in children with atopic dermatitis.' J. Pediatr. 145(5):612-616, 2004.*
Akira Iwamoto et al., "3Jl4pl0 Ichiao Chushutsubutsu no IgE Kotai Sansei Yokusei no Mechanism", Japan Society for Bioscience, Biotechnology, and Agrochemistry 2011 Nendo Taikai Koen Yoshishu, Mar. 5, 2011, vol. 2011, p. 215, particularly, col. of [Object], lines 1 to 3.
Akira Iwamoto et al., "AOIp In vitro Allergy Model ni Okeru Ichigo Chushutsubutsu no Ko- Allergy Sayo", Japan Society for Bioscience, Biotechnology, and Agrochemistry, Chushikoku Nishi Nippon Shibu, Japan Society of Nutrition and Food Science, Kyushu 022Okinawa Shibu, The Japanese Society for Food Science and Technology, Nishi Nippon Shibu, 2009 Nendo Godo Okinawa Taikai Koen Yoshishu, Oct. 30, 2009, p. 59, col. of [Object], [Method022Result].
Itoh, T., et al., Inhibitory effects of flavonoids isolated from Fragaria ananassas Duch on IgE-mediated degranulation in rat basophilic leukemia RBL-2H3, Bioorganic & Medicinal Chemistry, Aug. 1, 2009, vol. 17, No. 15, p. 5374-5379, particularly, p. 376, right column, col. of 4.1. Isolation of flavonoids and their chemical structures, line 1.
Kawahara, K. et al., "Effective induction and acquisition of human monoclonal IgE antibodies reactive with house-dust mite extract", Journal of Immunological Methods 233 (2000)33-40.
Khan, A.A. , et al . , Molecular cloning, characterization, and expression analysis of two class II chitinase genes from the strawberry plant, Plant Science, Mar. 2004, vol. 166, No. 3, p. 753-762, particularly, p. 759.
Masahiro Terauchi et al., "Antioxidant Activity and Anti-allergic Activity of Fragaria x ananassa Leaf", The Japanese Journal of Pharmacognosy, Feb. 20, 2007, vol. 61, No. 1, pp. 18 to 23, particularly, p. 19, left column, paragraph of Jikken Zairyo, table 1.
PCT/JP2012/060389 International Search Report mailed Jul. 24, 2012.
Van Der Ventel, M.L. , et al ., Differential responses to natural and recombinant allergens in a murine model of fish allergy, Molecular Immunology, Jan. 2011, vol. 48, No. 1, p. 637-646, particularly, Abstract, Results.
Yoshihisa Takahata et al., "Identification of Chicken Meat Proteins Detected with IgE Antibodies from Allergic Patients", Japanese poultry science, 2000, vol. 37, No. 4, pp. 228 to 233, particularly, abstract.
Supplementary European Search Report dated Sep. 16, 2014, in EP 12773893.8.
Suleimani et al., "Allergic rhinitis and its pharmacology," Pharmacology & Therapeutics, Jun. 1, 2007, 114(3):233-260.

* cited by examiner

*Primary Examiner* — Nora Rooney
(74) *Attorney, Agent, or Firm* — Foley & Lardner LLP

(57) ABSTRACT

This invention provides an anti-allergic substance that effectively inhibits allergic symptoms by inhibiting production of the IgE antibody associated with the development of allergies. Anti-allergic substances, pharmaceutical products (i.e., anti-allergic agents), and food (i.e., food with health-promoting benefits) containing strawberry-derived glyceraldehyde-3-phosphate do not cause side effects such as those caused by steroids, and such substances can be consumed through daily meals and can alleviate allergic symptoms.

1 Claim, 4 Drawing Sheets

ANTI-ALLERGIC SUBSTANCE, ANTI-ALLERGIC AGENT, AND FOOD

CROSS-REFERENCE TO RELATED APPLICATIONS

This application is a national phase of International Application PCT/JP2012/060389, filed Apr. 17, 2012, which was published on Oct. 26, 2012, as WO 2012/144501, which claims the benefit of Japanese application No. 2011-096512, filed Apr. 22, 2011. The respective contents of these applications are incorporated here by reference in their entirety.

TECHNICAL FIELD

The present invention relates to an anti-allergic substance, an anti-allergic agent, and a food. More particularly, the present invention relates to an anti-allergic substance that functions as a physiologically active substance for inhibiting IgE antibody production.

BACKGROUND ART

In recent years, the number of patients with urban diseases, such as pollen allergies and house dust allergies, has been rapidly increasing. In particular, 15% to 20% of the population in Japan is said to suffer from pollen allergies. In addition, it is said that the number of such patients will increase in the future, and that this problem will become more serious. Even though symptoms of pollen allergies significantly influence patients' lives in the form of, for example, a runny nose, cough, or an itchy eye, such symptoms are not life-threatening, and many patients are thus forced to merely endure such symptoms. In addition, a variety of therapeutic techniques have been attempted in hospitals, although no definite therapeutic techniques have been found. At present, accordingly, anti-inflammatory steroids are used to alleviate severe symptoms.

Since steroids are hormones in living organisms, steroidal anti-inflammatory agents with strong anti-inflammatory effects exert physiological effects as hormones in vivo, in addition to their anti-inflammatory effects. Accordingly, strong side effects thereof have been pointed out, and use of steroids should be strictly supervised by doctors. In addition, many patients are concerned about such side effects. Unlike medicine, food with health-promoting benefits is not intended to treat diseases. However, introduction of such food into a regular diet is expected to easily realize disease prevention or symptom alleviation. Accordingly, high expectations are placed on such food as a means of realizing an improvement in patients' quality of life.

Allergic diseases, such as pollen allergies and atopic dermatitis, are referred to as type I hypersensitivity or immediate hypersensitivity in the medical field, and many researchers have been studying the pathogenic mechanisms thereof. To date, the following has been elucidated. First, pollens that are allergens inhaled by breathing bind to IgE antibodies as the immune responses in vivo. Further, pollen-IgE antibody conjugates bind to mast cells. Thus, chemicals such as histamines and leukotrienes are released from the mast cells, and such substances cause inflammations in the nose, the eyes, and the respiratory tract. That is, IgE antibodies trigger allergies against the invasion of the body by pollens. Thus, an in vivo reduction of IgE antibodies would result in the inhibition of allergy symptoms.

The present inventors had constructed an experimental system capable of reproducing IgE antibody production in vitro by conducting in vitro culture of immunocytes associated with IgE antibody production in vivo. The present inventors had independently constructed a culture system involving the use of human peripheral blood lymphocytes simulating the in vivo kinetics of human allergies and identified ingredients exerting anti-allergic effects from among food ingredients. Unlike conventional test techniques involving the use of a large number of test animals such as mice, the aforementioned technique allows the simultaneous testing of several hundred types of specimens over a culture period of about 10 days, and such technique is thus highly efficient. Because of the use of human cells, in addition, when an effective ingredient is found among the searched factors, such ingredient is highly likely to exert effects in vivo, and the time required for screening can also be shortened. Furthermore, the interaction between the screened factor and a cell may be examined so as to elucidate the action mechanism of such factor at the cellular level. Accordingly, this technique has many advantages, such that functions of food can be evaluated from a scientific perspective (Non-Patent Document 1).

PRIOR ART DOCUMENTS

Non-Patent Documents

Non-Patent Document 1: J. Immunol. Methods 233, 2000, pp. 33-40, issued by Elsevier).

SUMMARY OF THE INVENTION

Object to be Attained by the Invention

While continuous administration of steroidal anti-inflammatory agents gives rise to side effects as described above, existing food products aimed at alleviation of such symptoms through a regular diet were not sufficiently effective.

The present inventors had constructed the experimental system described above and had been able to screen for substances capable of inhibiting IgE production with the use of such experimental system.

Accordingly, it is an object of the present invention to identify a substance that is capable of treatment of allergic diseases or alleviation of allergic symptoms via inhibition of IgE production and that is sufficiently safe for long-term consumption without causing side effects such as those caused by steroids, thereby providing an anti-allergic substance containing such substance. It is another object of the present invention to provide an anti-allergic agent comprising the identified substance (i.e., a pharmaceutical product) and a food product referred to as a "food with health-promoting benefits" having anti-allergic effects.

Means for Attaining the Objects

In order to attain the above objects, the present inventors have conducted studies with the use of the IgE antibody producing experimental system, so as to screen for a substance capable of inhibiting IgE production, with the addition of a variety of strawberry extracts to the culture system. As a result, it was discovered that a strawberry crude extract had the effect of inhibiting IgE antibody production. In addition, the purification was carried out for the crude extract using the effect of inhibiting IgE antibody production as an indicator and consequently it was discovered with the use of a purified fraction product that an ingredient exhibiting the highest activity was glyceraldehyde-3-phosphate dehydrogenase (GAPDH) which was a metabolizing enzyme. In order to further advance the research, rabbit-derived glyceraldehyde-3-phosphate dehydrogenase was also examined as an ingredient derived from another organism, since glyceraldehyde-3-phosphate dehydrogenase exists in a variety of organisms. As a result, it was found that the rabbit-derived glyceraldehyde-3-phosphate dehydrogenase also exerted effect of inhibiting IgE antibody production, as did the strawberry-derived glyceraldehyde-3-phosphate dehydrogenase. It was ascertained that the glyceraldehyde-3-phosphate dehydrogenase had the effect of inhibiting IgE antibody production based on the above finding.

According to the first aspect of the present invention, glyceraldehyde-3-phosphate dehydrogenase is contained as an anti-allergic substance that inhibits IgE antibody production.

Since such ingredient is expected to be easily ingestible through a regular diet, it is preferably provided in the form of a food. In particular, strawberries, in which the above-mentioned ingredient was discovered for the first time, have strong food preference, and they are also highly popular in the market. In addition, strawberries are eaten fresh, and they are also used for processed food products, such as beverage products, candies, or frozen confections. Accordingly, use of strawberries for food products is very advantageous.

According to the second aspect of the present invention, a composition comprising glyceraldehyde-3-phosphate dehydrogenase is in the form of food.

According to the third aspect of the present invention, glyceraldehyde-3-phosphate dehydrogenase is incorporated into an anti-allergic agent as an active ingredient, and the resulting agent can be used for allergy prevention and treatment.

It should be noted that organisms containing glyceraldehyde-3-phosphate dehydrogenase having anti-allergic effects are not limited to strawberries, and such enzyme is present in all living organisms. While this enzyme has been known to be associated with the metabolism of organisms, the anti-allergic effects thereof have not drawn attention as discovered in the present invention. However, the enzyme, which is included in a wide variety of other organisms, is considered to have anti-allergic effects as an ingredient for inhibiting IgE antibody production. Accordingly, the origin of glyceraldehyde-3-phosphate dehydrogenase is not necessary limited to strawberries, even when they are used for food, and such enzyme may be derived from any adequate organism as a food ingredient. When an anti-allergic agent is a pharmaceutical product for oral administration, the origin of the enzyme of interest is likely to be selected based on a perspective similar to that used for food. However, the origin of such enzyme may be adequately selected from among a wide variety of organisms in accordance with intended use, including in the case of cosmetic products comprising anti-allergic substances.

Effects of the Invention

According to the present invention, glyceraldehyde-3-phosphate dehydrogenase was identified as an ingredient having the anti-allergic effects (i.e., the effect of inhibiting IgE production). Therefore, the present invention can provide an anti-allergic substance that is capable of treatment of allergic diseases or alleviation of allergic symptoms and is sufficiently safe for long-term consumption without causing side effects such as those caused by steroids. In addition, the present invention can provide an anti-allergic agent (i.e., a pharmaceutical product) and food with health-promoting benefits.

EMBODIMENTS FOR CARRYING OUT THE INVENTION

Figure 1:
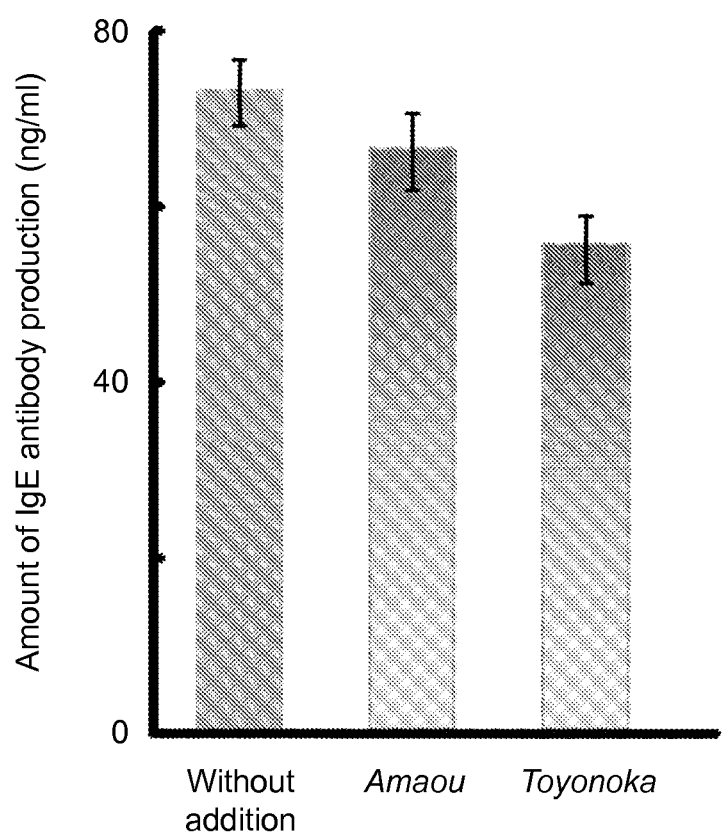
FIG. 1 shows a chart demonstrating the effects of the strawberry cultivars "Amaou" and "Toyonoka" on the inhibition of IgE antibody production.

In the present invention, glyceraldehyde-3-phosphate dehydrogenase may be an enzyme originating from any of a variety of organisms. It is not necessary that the amino acid composition of such enzyme completely match that of the glyceraldehyde-3-phosphate dehydrogenase originating from strawberries.

In general, strawberries are widely eaten raw, and they are also used for processed food products. This indicates that strawberries are approved to be highly safe food items that have no adverse effects on the human body. Accordingly, a strawberry extract mainly composed of glyceraldehyde-3-phosphate dehydrogenase used in the present invention is safe for consumption.

Glyceraldehyde-3-phosphate dehydrogenase used in the present invention can be obtained by subjecting the strawberry flesh of "Amaou" or "Toyonoka" to extraction with an aqueous solvent. From the viewpoint of the applicability of the extract to a food or cosmetic product, use of an aqueous solvent is preferable for safety reasons.

The amount of the ingredient to be consumed should be individually determined in accordance with conditions such as the age, sex, and symptoms of each allergy patient. Such amount is preferably 5% to 100% relative to the amount of the composition by weight.

The composition of the present invention can be used for a pharmaceutical or food product, for example. In the case of a pharmaceutical product, oral administration thereof is preferable. Accordingly, the composition can be mixed with a substance that is commonly used as an additive for a medicine, such as sorbitol, gelatin, lactose, glucose, starch, or citric acid, to prepare a pharmaceutical product. Alternatively, the composition of the present invention can be incorporated into a solid, liquid, gel, or other form of a food product. Since the composition can be incorporated into a food product by any known technique, it can be incorporated into, for example, ice cream, chocolate, candy, or a soft drink.

Hereafter, the examples of the present invention are described, although the present invention is not limited to these examples.

Example 1

Samples

The varieties of strawberry samples used in the example are commercially available strawberry cultivars "Amaou" and "Toyonoka."

[Separation of Lymphocytes]

In order to obtain human peripheral blood lymphocytes, the peripheral blood samples of healthy subjects were separated via density gradient centrifugation. First, the peripheral blood samples were obtained from healthy subjects and introduced into heparin-containing vacuum tubes. In each tube, 5 ml of the peripheral blood sample was superposed on 4 ml of the blood separator (Ficoll; GE Healthcare), which had been fractionated in a 15-ml centrifugal tube in advance, while refraining from causing turbulence on the liquid surface, and centrifugation was then carried out at 400×g for 30 minutes. The uppermost blood plasma layer was collected and stored at −24° C. Subsequently, lymphocytes existing between the blood plasma layer and the Ficoll layer were collected, washed in a synthetic basal medium (ERDF, Kyokuto Seiyaku), and centrifuged at 400×g for 5 minutes, followed by washing. This procedure was repeated three times. The obtained lymphocytes were cryopreserved at −85° C., thawed, and then washed in an ERDF medium before use.

[In vitro Allergy Onset Model Cells Culture System]

The human peripheral blood lymphocytes ($2.5 \times 10^6$ cells/ml) extracted from organisms, 10 mg/ml muramyl dipeptide (MDP; SIGMA) and 10 ng/ml interleukin-2, interleukin-4, and interleukin-6 (IL-2, IL-4, and IL-6; R&D) as immunostimulators, and 100 ng/ml (final concentration) *Cryptomeria japonica* pollen antigens (Cryj 1, Hayashibara) were introduced into the ERDF medium containing 5% fetal bovine serum (FBS, Trace) and 10% human blood plasma. Thus, an in vitro allergy model culture system was prepared. Major functions of the immunostimulators added are adjuvant activity that enhances the immune responses of MDP to antigens, acceleration of T cell growth and differentiation by IL-2, induction of IgE class switching by IL-4, and induction of B cell differentiation by IL-6. The human peripheral blood lymphocytes supplemented with the immunostimulators and Cryj 1 were fractionated to a 96-well plate at 200 ml/well, and culture was conducted in an incubator at 37° C. in the presence of 5% $CO_2$ for 10 days to induce IgE antibody production. The human blood plasma and the human peripheral blood lymphocytes in this culture system are derived from the same individual.

[Preparation of Strawberry Extract]

With the use of a PRO 250 homogenizer (PRO Scientific), strawberries were subjected to crushing at 6,000 rpm for 30 seconds. Strawberries were ice-cooled before crushing. Subsequently, the crushed strawberry product was mixed with the same amount of PBS, and the resultant was centrifuged at 8,300×g for 1 hour at 4° C. Thereafter, the supernatant was sterilized through a 0.22-μm filter to obtain a strawberry extract, and the resulting extract was added to the in vitro allergy model culture system to an amount that was 5% (v/v) thereof to examine the anti-allergic effects.

[Assay of Amount of IgE Antibody Production via ELISA]

The amount of IgE antibody produced in the culture supernatant was assayed via ELISA (i.e., the enzyme-linked immunosorbent assay). The goat anti-human IgE antibody (Biosource) was diluted 2,000-fold with carbonate buffer, and the diluted antibody was applied to a 96-well Immuno plate at 100 ml/well. After the plate was allowed to stand at 37° C. for 1 hour, a solution of bovine serum albumin (BSA; ICN) diluted to 1% in phosphate buffer (PBS) (i.e., a 1% BSA/PBS solution) was dispenced to the plate at 300 ml/well in order to block the wells for prevention of non-specific reactions. Thereafter, the resultant was allowed to stand at 37° C. for 1 hour, the culture supernatant containing the IgE antibody to be quantified was diluted to one-eighth of its original concentration with 1% BSA/PBS, and the resultant was dispensed to the plate at 50 ml/well. Also, standard solutions prepared by performing a ⅓ dilution of the culture supernatant from the concentration at 1 mg/ml to that at ⅟₃₈ mg/ml were applied to the plate at 50 ml/well, and the plate was then allowed to stand at 37° C. for 1 hour. Thereafter, the biotin-labeled goat anti-human IgE antibody (Biosource) was diluted 2,000-fold with 1% BSA/PBS, dispensed to the plate at 100 ml/well, and then allowed to stand at 37° C. for 1 hour. Thereafter, streptoavidin (Funakoshi) labeled with horseradish-derived peroxidase was diluted 1,000-fold with a 1% BSA/PBS solution, the resultant was dispensed to the plate at 100 ml/well, and the plate was allowed to stand at 37° C. for 1 hour. A color-developing solution; i.e., a solution containing 0.006% $H_2O_2$-0.2 M citrate buffer (pH 4.0), 6 mg/ml ABTS-$(NH_4)_2$ (Wako), and ultrapure water at 10:1:9, was dispensed to the plate at 100 ml/well, and the absorbance at 414 nm was measured 30 minutes later. In the time between reactions, the plate was washed three times with a solution comprising polyethylene (20) sorbitan monolaurate (Tween 20, Wako) diluted to 0.05% in PBS. FIG. 1 shows a chart demonstrating the effects of the strawberry cultivars "Amaou" and "Toyonoka" on the inhibition of IgE antibody production. FIG. 1 shows the anti-allergic effects tested in the manner described above.

Example 2

Identification of Active Fraction

The strawberry extract prepared in Example 1 was purified using anion-exchange resin (DEAE-6505) using the effect of inhibiting IgE antibody production as the indicator. As a result, an active ingredient was eluted into a non-adsorbed fraction. Further, a fraction containing the active ingredient was purified with a 0.5 M sodium chloride solution using cation-exchange resin (SP550C). Furthermore, a fraction subjected to ultrafiltration with a molecular weight cut-off of 3,000 Da was inspected and the resulting effects of inhibiting IgE production were observed. Thus, protein analysis was carried out. As a result, the fraction was found to be a protein of approximately 36 KDa comprising the amino acid sequence (AKIKIGINGF) from the N-terminus of the protein. As a result of screening of a protein database, the fraction was found to match the glyceraldehyde-3-phosphate dehydrogenase.

[Confirmation of glyceraldehyde-3-phosphate dehydrogenase Activity]

Figure 2:
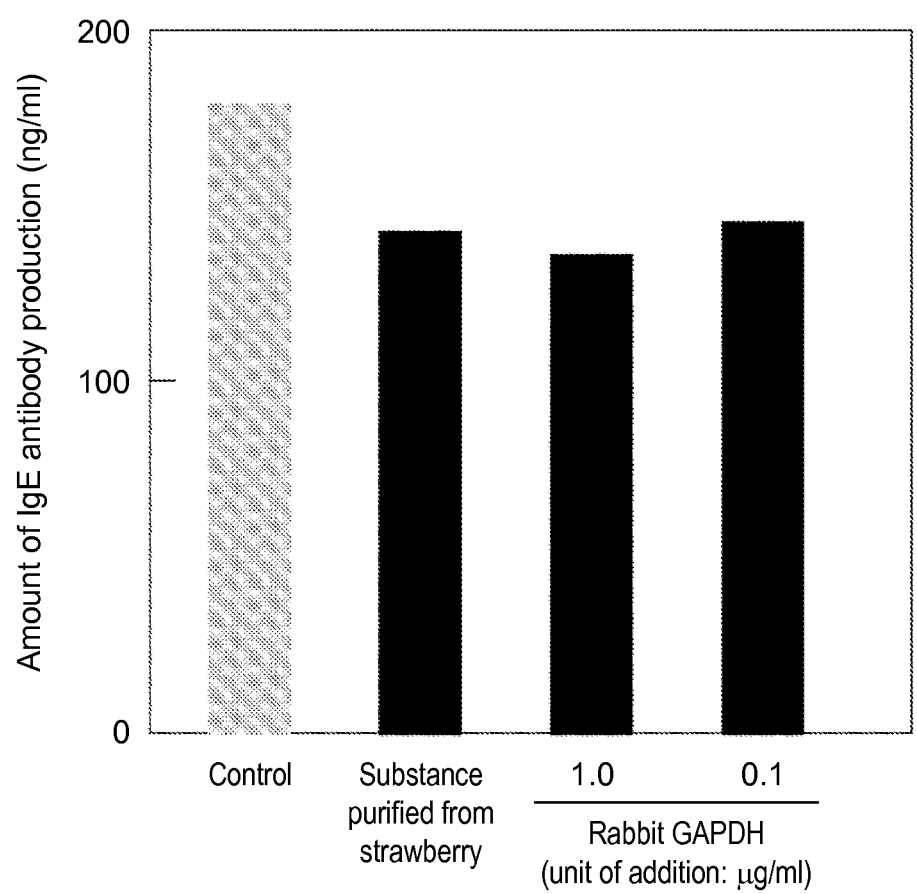
FIG. 2 shows a chart demonstrating a comparison of the effects of inhibiting IgE antibody production between that of a substance purified from strawberry and that of a rabbit-derived glyceraldehyde-3-phosphate.

Glyceraldehyde-3-phosphate dehydrogenase is a metabolizing enzyme existing in a wide variety of organisms. Thus, activity of the glyceraldehyde-3-phosphate dehydrogenase originating from the purified preparation of strawberry was compared with that of a commercially available general reagent (i.e., a rabbit-derived glyceraldehyde-3-phosphate dehydrogenase sample). As a result, the rabbit-derived glyceraldehyde-3-phosphate dehydrogenase was found to have similar effects of inhibiting IgE production. Since the glyceraldehyde-3-phosphate concentration in the substance purified from strawberry ranged from 0.1 to 1 μg/ml, the rabbit-derived glyceraldehyde-3-phosphate sample was subjected to comparison at the concentration of 0.1 μg/ml and 1 μg/ml (each corresponding to the lower limit and the upper limit, respectively). FIG. 2 shows a chart demonstrating a comparison of the effects of inhibiting IgE antibody production between a substance purified from strawberry and rabbit-derived glyceraldehyde-3-phosphate. FIG. 2 shows the results thus verified. In FIG. 2, a control is provided for comparison, and the substance purified from Toyonoka is the substance purified from strawberry according to the invention of the present application. The vertical axis indicates the amount of IgE antibody production. While the control sample inhibited the production of the IgE antibody at 180 ng/ml, the substance purified from strawberry inhibited such production at 140 ng/ml. That is, the effect of the substance purified from strawberry on the inhibition of IgE antibody production was higher by approximately 20% than that of the control sample. The rabbit-derived glyceraldehyde-3-phosphate also inhibited the production of the IgE antibody at approximately 140 ng/ml, which was substantially the same level as that achieved with the substance purified from strawberry and approximately 20% higher than that of the control sample. Thus, glyceraldehyde-3-phosphate was found to have the effect of inhibiting IgE antibody production.

Example 3

Physiological Activity of glyceraldehyde-3-phosphate dehydrogenase

In order to assay the physiological activity of an anti-allergic ingredient in the strawberry extract, mouse models of atopic dermatitis (NC/Nga mice, Charles River Japan) and BALB/C mice induced to develop allergic rhinitis (Charles River Japan) were employed in order to inspect improvement in symptoms via feeding.

Mouse models of atopic dermatitis were induced to develop dermatitis via application of picryl chloride. Specifically, 5 g of picryl chloride was introduced into a conical flask, 40 ml of 100% ethanol was added thereto, and the flask was slowly heated to melt picryl chloride with gentle mixing. Heating was terminated when the color of the solution turned yellow, 10 ml of distilled water at ice temperature was added, and the flask was introduced into ice immediately thereafter, followed by crystallization of picryl chloride. The supernatant was allowed to pass through a glass filter (pore size: 20 to 30 μm), and unfiltered crystals were collected. The collected crystals were suspended in 200 ml of 50% ethanol, the suspension was allowed to stand for several minutes, the resultant was allowed to pass through a glass filter washed with 100% ethanol, and unfiltered crystals were collected. The collected crystals were suspended in 200 ml of 50% ethanol, the suspension was allowed to stand for several minutes, the resultant was allowed to pass through a glass filter washed with 100% ethanol, and unfiltered crystals were collected. The collected crystals were placed on filter paper, and the filter paper was folded so as to enclose the crystals. The filter paper was wrapped in aluminum foil or the like for light shielding, and the filter paper was dried at room temperature until the following morning. The sample was dissolved in olive oil at a concentration of 0.8% to 1.0% as a purified picryl chloride product, the mouse body was partially shaved to expose the skin, and the solution was applied to the exposed skin to induce the mice to develop atopic dermatitis.

Mouse models of allergic rhinitis were prepared by dissolving the purified *Cryptomeria japonica* pollen antigen in phosphate buffered saline containing aluminum hydroxide at 50 μg/ml, injecting the resulting antigen solution intraperitoneally into mice, and initiating once-a-day intranasal administration of the antigen solution 5 days thereafter to induce rhinitis.

Figure 3:
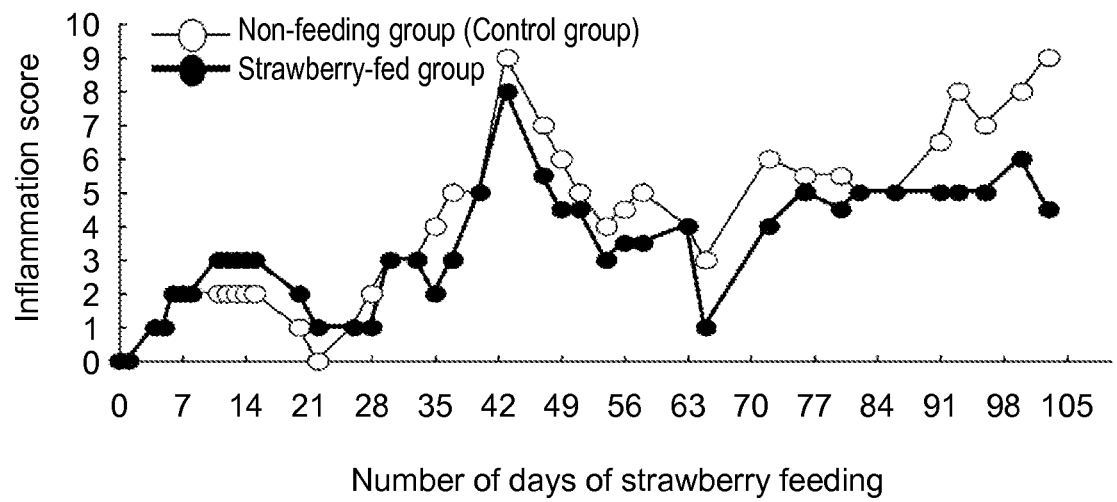
FIG. 3 shows a chart demonstrating the anti-allergic effects of a strawberry composition tested using mouse models of atopic dermatitis.

In order to evaluate the effects of symptom improvement, the mouse models of atopic dermatitis were scored based on the area of dermatitis (scores: 1: an area of 0.5 $cm^2$; 2: 1.0 $cm^2$; 3: 2.0 $cm^2$; and 4: 3.0 $cm^2$). FIG. 3 shows a chart demonstrating the anti-allergic effects of a strawberry composition tested using mouse models of atopic dermatitis. The results are shown in FIG. 3. In the chart shown in FIG. 3, the horizontal axis indicates the number of days during which the strawberry extract had been consumed and the vertical axis indicates the scores for dermatitis described above. A higher score indicates a higher degree of inflammation. While the degrees of inflammation were generally similar between the control group and the group that had been fed the strawberry extract, the inflammation scores of the group that had been fed the strawberry extract began to become constantly lower than that of the control group about 21 days after the initiation of feeding. Thus, inflammation was alleviated as a result of strawberry consumption.

While dermatitis developed after the initiation of immunization and the degree of inflammation became worsened day by day, the inflammation began to heal in the group of mice that had been fed the strawberry extract. When the experiment was terminated, symptom improvement was observed to such an extent that the inflammation score had been reduced to half of the score at the initiation of the experiment.

Figure 4:
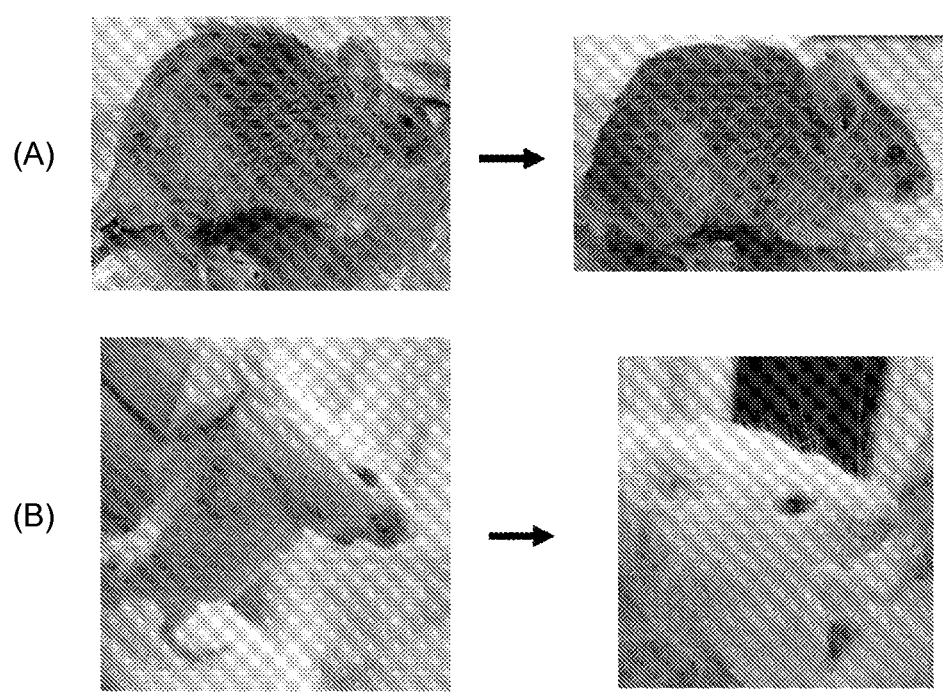
FIG. 4 shows a photograph showing the anti-allergic effects of a strawberry composition tested using mouse models of atopic dermatitis and those of rhinitis.

FIG. 4 shows a photograph showing the anti-allergic effects of a strawberry composition tested using mouse models of atopic dermatitis and those of rhinitis. FIG. 4(A) shows photographs of mouse models of atopic dermatitis and FIG. 4(B) shows photographs of mouse models of rhinitis. The symptoms shown in the left photographs were improved to the symptoms shown in the right photographs as a result of consumption of the strawberry extract. In the case of mouse models of atopic dermatitis, the dermatitis was alleviated as a result of consumption of strawberry. In the case of mouse models of allergic rhinitis, hair loss was observed around the nose of mice in the control group; however, the mice in the group that had been fed the strawberry extract did not develop rhinitis, and they did not experience hair loss around the nose.

According to the present invention, food products having anti-allergic effects may be any food products, provided that such food products contain glyceraldehyde-3-phosphate dehydrogenase, which originates from a variety of organisms (including plants and animals) and is capable of inhibiting IgE antibody production. In addition to the improved strawberry cultivars, other improved existing fruit or vegetable cultivars are applicable. Further, new cultivars that have been improved so as to impart a variety of desirable features are also applicable. This can significantly contribute to the development of food products having anti-allergic effects in the industry for food with health-promoting benefits.

The invention claimed is:
1. A method of treating allergic disease, comprising orally administering a purified glyceraldehyde-3-phosphate dehy- drogenase to a patient who has atopic dermatitis or allergic rhinitis, thereby inhibiting IgE antibody production in said patient.

* * * * *